US00PP32736P2

(12) United States Plant Patent
Horvath

(10) Patent No.: US PP32,736 P2
(45) Date of Patent: Jan. 5, 2021

(54) *PANICUM VIRGATUM* PLANT NAMED 'PRAIRIE DOG'

(50) Latin Name: *Panicum virgatum*
Varietal Denomination: Prairie Dog

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 16/602,901

(22) Filed: Dec. 23, 2019

(51) Int. Cl.
*A01H 5/12* (2018.01)
*A01H 6/46* (2018.01)

(52) U.S. Cl.
USPC ..... Plt./384
CPC ..... *A01H 6/4642* (2018.05)

(58) Field of Classification Search
USPC ..... Plt./384
CPC ..... A01H 6/4642; A01H 5/12; A01H 5/02
See application file for complete search history.

*Primary Examiner* — Keith O. Robinson

(57) ABSTRACT

A new, *Panicum virgatum* plant as described and illustrated, characterized by a more upright plant with a height of 103 cm.

1 Drawing Sheet

Latin name: *Panicum virgatum.*
Cultivar name: 'Prairie Dog'.

BACKGROUND OF THE INVENTION

The present invention relates to a new form of *Panicum virgatum* plant named 'Prairie Dog'. 'Prairie Dog' is a seedling of *Panicum virgatum*, characterized by an upright plant with a height of 110 cm, and clean greyed-green color foliage. The new plant was grown as a seedling from a mix of named and unnamed open pollinated *Panicum virgatum*, by the inventor at a wholesale perennial nursery in Hebron, Ill. USA in 2016. The selection of this plant was due to its upright stems, relatively shorter height of 110 cm, and clean greyed-green colored foliage. Asexual, vegetative division propagation has been the only means of reproduction. Propagation has taken place at Hebron, Ill. since 2017. In 2018 we planted 300 plants in 1 gallon pots. To date these plants have remained uniform in height, and foliage color. The new *Panicum virgatum* has shown to be stable and identical in reproduction to the parent after making over 1000 vegetative divisions from 2017 to 2019. No plants of the new *Panicum virgatum* have been sold in this country, or anywhere in the world, prior to the filing of this application, nor has any disclosure of the new plant been made prior to the filing of this application with the exception of that which was disclosed by the inventor within one year of filing of this application and was derived directly from the inventor.

SUMMARY OF THE INVENTION

In the following description, color references are made to The Royal Horticultural Society Colour Chart (copyright 2001). The new *Panicum virgatum* plant named 'Prairie Dog' has shown the characteristics of upright plants with height of 110, and clean greyed-green colored foliage to be unique and stable. For purpose of the comparison the new plant will be referred to as 'Prairie Dog'.

Plants of 'Prairie Dog' can be compared to plants of *Panicum virgatum* 'Northwind', not patented. 1. 'Prairie Dog' has a height of 110 cm compared to the height of

*Panicum virgatum* 'Northwind' which has an average height of 180 cm. 2. 'Prairie Dog' has a foliage color of greyed-green 189 A compared to *Panicum virgatum* 'Northwind' which has foliage color of green.

Plants of 'Prairie Dog' can be also be compared to plants of *Panicum virgatum* 'Heavy Metal' not patented. 1. 'Prairie Dog' has a height of 110 compared to the height of *Panicum virgatum* 'Heavy Metal' which has an average height of 120 cm. 2. 'Prairie Dog' has a foliage color of green 189 A compared to *Panicum virgatum* 'Heavy Metal' which has foliage color that is, blue-green. 'Prairie Dog' has a more upright habit while the *Panicum virgatum* 'Heavy Metal' has an open habit. 3. 'Prairie Dog' has a larger inflorescence to 30 cm long and 13 cm wide compared to *Panicum virgatum* 'Heavy Metal' which has an inflorescence that is less substantial.

DESCRIPTION OF PHOTOGRAPHS

Figure 1:
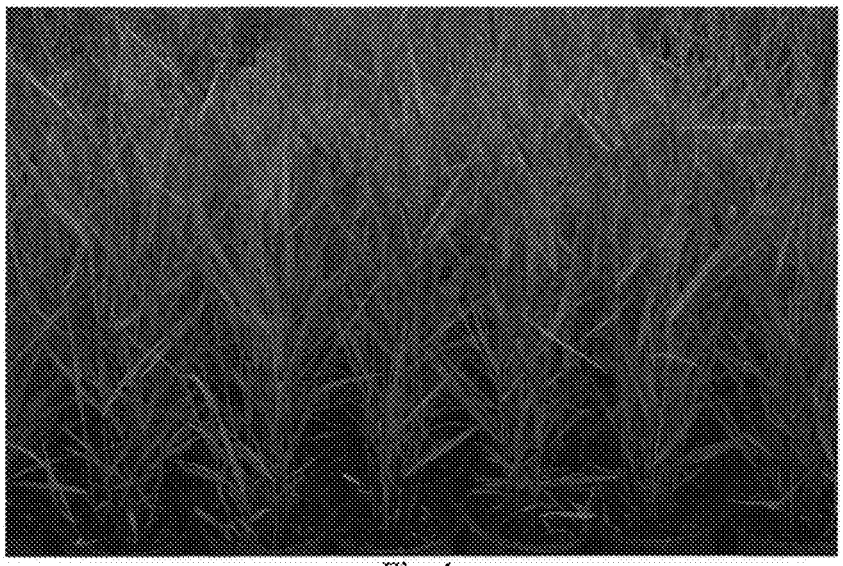

FIG. 1. Shows potted plants blooming in August.

Figure 2:
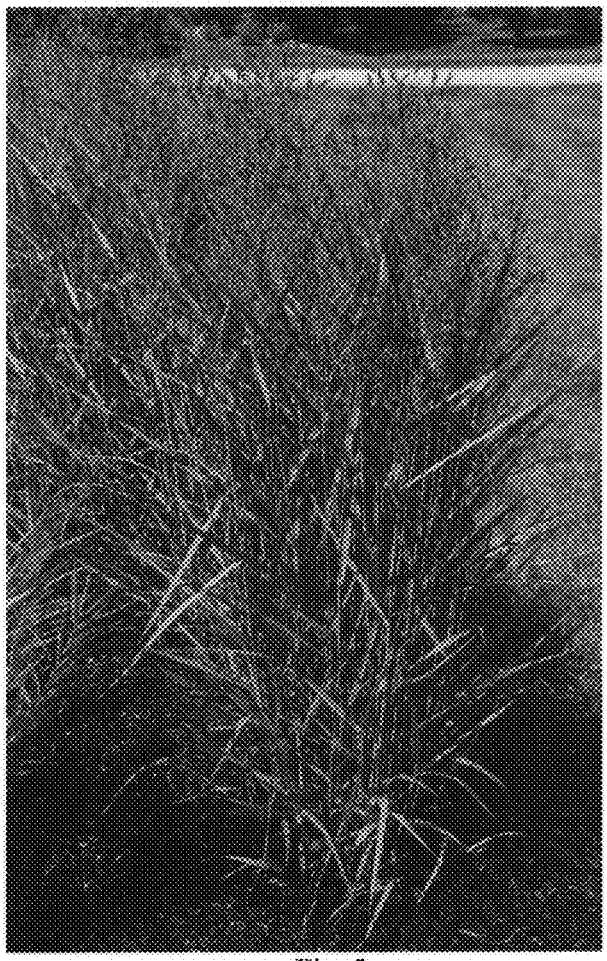

FIG. 2. Shows a mature plant in September with greyed-green foliage color.

DETAILED BOTANICAL DESCRIPTION

In the following description, color references are made to The Royal Horticultural Society Colour Chart. The plant herein described is an established 2 year old plant growing in a garden, grown in full sun and irrigated in Hebron, Ill. USA. Measurements and numerical values represent averages of typical plants.

Botanical classification: *Panicum virgatum* cultivar 'Prairie Dog'.

Parentage: Both male and female are *Panicum virgatum* unknown seedlings.

Propagation: Vegetative division.

Plant description: Overall habit of the new *Panicum virgatum* is clumping with upright culms topped by green 138 B colored flowers beginning in August. Vigor is moderate. Plant height: 110 cm, Plant width: 45 cm.

Foliage and stems:

*Foliage description*.—Glabrous, flat blade, sheathed from node of attachment to ligule, linear.

*Type*.—Deciduous, grass growing in culms.

*Shape*.—Blade. Number of blades — typically 5 blades per stem.

*Sheath*.—17 mm wide, 19 cm long, surface — glabrous.

*Ligules*.—Up to 1 mm long and up to 6 mm wide.

*Blade*.—10 mm wide, up to 30 cm long.

*Adaxial leaf description*.—Leaf color is 189 A throughout the season.

*Abaxial leaf description*.—Leaf color is 189 A throughout the season.

*Veins*.—parallel, same color, 189 A, as surrounding leaf on top, midrib on the bottom of leaf is 0.5 mm wide and 189 A in color.

*Culm description*.—Erect, cylindrical, glabrous, two-thirds enclosed by leaf sheath, typically up to 5 leaves or nodes.

*Culm dimensions*.—4 mm wide, 70 cm long without the panicle, 100 cm including the panicle.

*Length of internodes*.—Average 10 cm. Color of the internodes is 138 A and B.

*Number of culms per clump*.—50 and 250 nodes per plant.

*Node description*.—Cylindrical. Number of nodes per culm — Average 5.

Flower inflorescence:

*Inflorescence type*.—Finely branched, terminal panicle, one panicle per culm, beginning in early August and remaining into winter.

*Panicle*.—Pyramidal, about 30 cm long and 12 cm wide, overall color 191 B and C with some parts N187 B.

*Rachis*.—Terete, branched, glabrous, glaucous 1-2 mm wide at the base and up to 30 cm long, branches 8-10 cm long and less than 1 mm diameter held at about a 60 degree angle above horizontal, color 138 B.

*Pedicel*.—Terete, 3-5 cm long and less than 1 mm diameter, color 138 B.

*Rachilla*.—6 mm long, and less than 1 mm in diameter, color 138 B.

*Spikelet*.—Usually has two flowers, both 1-2 mm wide and 3 cm long.

*Lower glume*.—1-2 mm wide, 3 mm long, color 138 B.

*Lemma*.—Outer and inner — both, 2 mm, 3 mm long, color 138 B.

*Flower number*.—Average 450 per culm.

*Gynoecium*.—Stigma — 2, color 191 B and C with N187 B.

*Androecium*.—Anthers — 2, color is 168 A. Pollen — color 168 A.

*Anther size*.—3 mm long by 1 mm wide, color 168 A.

*Fruit or seeds*.—Color is 157 A, size is 2 mm wide, 3 mm long. Scent — no scent.

*Roots*.—stiff, fibrous, and freely branching.

*Hardiness*.—United States Department of Agriculture Zones 4-9.

*Disease resistance*.—Plants are not more or less susceptible to any major pests or diseases.

I claim:

1. A new, distinct *Panicum virgatum* plant as described and illustrated, characterized by an upright plant with a height of 103 cm.

* * * * *